(12) United States Patent
Wehrman et al.

(10) Patent No.: US 8,211,655 B2
(45) Date of Patent: Jul. 3, 2012

(54) WILD-TYPE RECEPTOR ASSAYS

(75) Inventors: Thomas S. Wehrman, Mountain View, CA (US); William Raab, San Francisco, CA (US); Chin Yee Loh, Kensington, CA (US)

(73) Assignee: Discoverx Corporation, Fremont, CA (US)

( * ) Notice: Subject to any disclaimer, the term of this patent is extended or adjusted under 35 U.S.C. 154(b) by 91 days.

(21) Appl. No.: 12/704,399

(22) Filed: Feb. 11, 2010

(65) Prior Publication Data
US 2010/0203555 A1   Aug. 12, 2010

Related U.S. Application Data

(60) Provisional application No. 61/152,124, filed on Feb. 12, 2009.

(51) Int. Cl.
| G01N 33/567 | (2006.01) |
| C07K 14/705 | (2006.01) |
| C07K 19/00 | (2006.01) |
| C12N 15/62 | (2006.01) |

(52) U.S. Cl. ....... 435/7.2; 435/7.21; 435/69.7; 436/501; 536/23.4

(58) Field of Classification Search ................. None
See application file for complete search history.

(56) References Cited

U.S. PATENT DOCUMENTS

| 5,272,071 | A | 12/1993 | Chappel et al. |
| 5,578,461 | A | 11/1996 | Sherwin et al. |
| 7,135,325 | B2 | 11/2006 | Naqvi et al. |
| 7,235,374 | B2 | 6/2007 | Palmer et al. |
| 7,361,641 | B2 | 4/2008 | Calos |
| 2003/0092070 | A1 | 5/2003 | Zhao et al. |
| 2003/0175836 | A1 | 9/2003 | Blau et al. |
| 2005/0287522 | A1 | 12/2005 | Blau et al. |
| 2007/0275397 | A1 | 11/2007 | Wehrman |

FOREIGN PATENT DOCUMENTS
WO   9309222 A2   5/1993

OTHER PUBLICATIONS

Keith E. Langley, et al., "Molecular Basis of Beta-Galactosidase Alpha-complementation," Proc. Nat'l Acad. Sci. USA, Apr. 1975, vol. 72, No. 4, 1254-1257.
Michael J. Wagner, et al., "Nucleotide sequence of the thymidine kinase gene of herpes simplex virus type 1," Proc. Natl. Acad. Sci. U.S.A., Mar. 1981, vol. 78, No. 3, 1441-1445.
Mark M. Hammer, et al., "A novel enzyme complementation-based assay for monitoring G-protein-coupled receptor internalization," FASEB J., Dec. 2007, vol. 21, 3827-3834.
Fadi F. Hamdan, et al., "Unraveling G Protein-couple Receptor Endocytosis Pathways Using Real-time Monitoring of Agonist-promoted Interaction between Beta-Arrestins and AP-2," J. Biol. Chem., Oct. 5, 2007, vol. 282, No. 40, 29089-29100.
Li-Fong Seet, et al., "Endofin recruits clathrin to early endosomes via TOM1.," J. Cell. Sci., 2005, 118:575-87. Epub 2005 doi: 10.1242/jcs.01628.
Gail A. Robertson, "Endocytic control of ion channel density as a target for cardiovascular disease," J. Clin. Invest., Sep. 2009, vol. 119, No. 9, 2531-2534.
Sanchita Mukherjee, et al., "Vesicular Trafficking of Tyrosine Kinase Receptors and Associated Proteins in the Regulation of Signaling and Vascular Function," Circ Res., Mar. 31, 2006, 743-756; doi: 10.1161/01. RES.0000214545.99387.e3.

*Primary Examiner* — John Ulm
(74) *Attorney, Agent, or Firm* — David J. Aston; Peters Verny, LLP (57) ABSTRACT

A method for determining ligand activation of receptors using cells expressing genetic constructs of a fusion protein of at least a binding domain of an auxiliary protein and a fragment of β-galactosidase, a fusion protein of an endosome-associated protein and a complementary fragment of β-galactosidase, and a wild-type receptor. The receptors are characterized by binding to the auxiliary protein-binding domain upon activation by an agonist and then endocytosing associated with an endosome to which the endosome-associated protein binds. Cells are incubated with a candidate ligand followed by lysis with a lysing medium comprising a substrate for the β-galactosidase. The enzyme product is then detected as a measure of the activation of the receptor.

15 Claims, 2 Drawing Sheets

SEQUENCE LISTING

```
<160> NUMBER OF SEQ ID NOS: 3

<210> SEQ ID NO 1
<211> LENGTH: 1421
<212> TYPE: PRT
<213> ORGANISM: Artificial Sequence
<220> FEATURE:
<223> OTHER INFORMATION: synthetic fusion protein

<400> SEQUENCE: 1

Met Gly Glu Lys Pro Gly Thr Arg Val Phe Lys Ser Ser Pro Asn
1               5                   10                  15

Cys Lys Leu Thr Val Tyr Leu Gly Lys Arg Asp Phe Val Asp His Leu
                20                  25                  30

Asp Lys Val Asp Pro Val Asp Gly Val Val Leu Val Asp Pro Asp Tyr
            35                  40                  45

Leu Lys Asp Arg Lys Val Phe Val Thr Leu Thr Cys Ala Phe Arg Tyr
        50                  55                  60

Gly Arg Glu Asp Leu Asp Val Leu Gly Leu Ser Phe Arg Lys Asp Leu
65                  70                  75                  80

Phe Ile Ala Thr Tyr Gln Ala Phe Pro Pro Val Pro Asn Pro Pro Arg
                85                  90                  95

Pro Pro Thr Arg Leu Gln Asp Arg Leu Leu Arg Lys Leu Gly Gln His
                100                 105                 110
```

```
Ala His Pro Phe Phe Phe Thr Ile Pro Gln Asn Leu Pro Cys Ser Val
        115                 120                 125

Thr Leu Gln Pro Gly Pro Glu Asp Thr Gly Lys Ala Cys Gly Val Asp
        130                 135                 140

Phe Glu Ile Arg Ala Phe Cys Ala Lys Ser Leu Glu Glu Lys Ser His
145                 150                 155                 160

Lys Arg Asn Ser Val Arg Leu Val Ile Arg Lys Val Gln Phe Ala Pro
                165                 170                 175

Glu Lys Pro Gly Pro Gln Pro Ser Ala Glu Thr Thr Arg His Phe Leu
            180                 185                 190

Met Ser Asp Arg Ser Leu His Leu Glu Ala Ser Leu Asp Lys Glu Leu
        195                 200                 205

Tyr Tyr His Gly Glu Pro Leu Asn Val Asn Val His Val Thr Asn Asn
        210                 215                 220

Ser Thr Lys Thr Val Lys Lys Ile Lys Val Ser Val Arg Gln Tyr Ala
225                 230                 235                 240

Asp Ile Cys Leu Phe Ser Thr Ala Gln Tyr Lys Cys Pro Val Ala Gln
                245                 250                 255

Leu Glu Gln Asp Gln Val Ser Pro Ser Ser Thr Phe Cys Lys Val
            260                 265                 270

Tyr Thr Ile Thr Pro Leu Leu Ser Asp Asn Arg Glu Lys Arg Gly Leu
        275                 280                 285

Ala Leu Asp Gly Lys Leu Lys His Glu Asp Thr Asn Leu Ala Ser Ser
        290                 295                 300

Thr Ile Val Lys Glu Gly Ala Asn Lys Glu Val Leu Gly Ile Leu Val
305                 310                 315                 320

Ser Tyr Arg Val Lys Val Lys Leu Val Val Ser Arg Gly Gly Asp Val
                325                 330                 335

Ser Val Glu Leu Pro Phe Val Leu Met His Pro Lys Pro His Asp His
            340                 345                 350

Ile Pro Leu Pro Arg Pro Gln Ser Ala Ala Pro Glu Thr Asp Val Pro
        355                 360                 365

Val Asp Thr Asn Leu Ile Glu Phe Asp Thr Asn Tyr Ala Thr Asp Asp
        370                 375                 380

Asp Ile Val Phe Glu Asp Phe Ala Arg Leu Arg Leu Lys Gly Met Lys
385                 390                 395                 400

Asp Asp Asp Tyr Asp Asp Gln Leu Cys Gly Gln Leu Phe Glu Leu Gly
                405                 410                 415

Gly Gly Gly Ser Gly Gly Gly Ser Leu Glu Ser Met Gly Val Ile
            420                 425                 430

Thr Asp Ser Leu Ala Val Val Ala Arg Thr Asp Arg Pro Ser Gln Gln
        435                 440                 445

Leu Arg Ser Leu Asn Gly Glu Trp Arg Phe Ala Trp Phe Pro Ala Pro
        450                 455                 460

Glu Ala Val Pro Glu Ser Trp Leu Glu Cys Asp Leu Pro Glu Ala Asp
465                 470                 475                 480

Thr Val Val Val Pro Ser Asn Trp Gln Met His Gly Tyr Asp Ala Pro
                485                 490                 495

Ile Tyr Thr Asn Val Thr Tyr Pro Ile Thr Val Asn Pro Pro Phe Val
            500                 505                 510

Pro Thr Glu Asn Pro Thr Gly Cys Tyr Ser Leu Thr Phe Asn Val Asp
        515                 520                 525

Glu Ser Trp Leu Gln Glu Gly Gln Thr Arg Ile Ile Phe Asp Gly Val
```

-continued

```
            530                 535                 540
Asn Ser Ala Phe His Leu Trp Cys Asn Gly Arg Trp Val Gly Tyr Gly
545                 550                 555                 560

Gln Asp Ser Arg Leu Pro Ser Glu Phe Asp Leu Ser Ala Phe Leu Arg
                565                 570                 575

Ala Gly Glu Asn Arg Leu Ala Val Met Val Leu Arg Trp Ser Asp Gly
                580                 585                 590

Ser Tyr Leu Glu Asp Gln Asp Met Trp Arg Met Ser Gly Ile Phe Arg
                595                 600                 605

Asp Val Ser Leu Leu His Lys Pro Thr Thr Gln Ile Ser Asp Phe His
                610                 615                 620

Val Ala Thr Arg Phe Asn Asp Asp Phe Ser Arg Ala Val Leu Glu Ala
625                 630                 635                 640

Glu Val Gln Met Cys Gly Glu Leu Arg Asp Tyr Leu Arg Val Thr Val
                    645                 650                 655

Ser Leu Trp Gln Gly Glu Thr Gln Val Ala Ser Gly Thr Ala Pro Phe
                660                 665                 670

Gly Gly Glu Ile Ile Asp Glu Arg Gly Gly Tyr Ala Asp Arg Val Thr
                675                 680                 685

Leu Arg Leu Asn Val Glu Asn Pro Lys Leu Trp Ser Ala Glu Ile Pro
690                 695                 700

Asn Leu Tyr Arg Ala Val Glu Leu His Thr Ala Asp Gly Thr Leu
705                 710                 715                 720

Ile Glu Ala Glu Ala Cys Asp Val Gly Phe Arg Glu Val Arg Ile Glu
                    725                 730                 735

Asn Gly Leu Leu Leu Leu Asn Gly Lys Pro Leu Leu Ile Arg Gly Val
                740                 745                 750

Asn Arg His Glu His His Pro Leu His Gly Gln Val Met Asp Glu Gln
                755                 760                 765

Thr Met Val Gln Asp Ile Leu Leu Met Lys Gln Asn Asn Phe Asn Ala
                770                 775                 780

Val Arg Cys Ser His Tyr Pro Asn His Pro Leu Trp Tyr Thr Leu Cys
785                 790                 795                 800

Asp Arg Tyr Gly Leu Tyr Val Val Asp Glu Ala Asn Ile Glu Thr His
                    805                 810                 815

Gly Met Val Pro Met Asn Arg Leu Thr Asp Asp Pro Arg Trp Leu Pro
                820                 825                 830

Ala Met Ser Glu Arg Val Thr Arg Met Val Gln Arg Asp Arg Asn His
                835                 840                 845

Pro Ser Val Ile Ile Trp Ser Leu Gly Asn Glu Ser Gly His Gly Ala
850                 855                 860

Asn His Asp Ala Leu Tyr Arg Trp Ile Lys Ser Val Asp Pro Ser Arg
865                 870                 875                 880

Pro Val Gln Tyr Glu Gly Gly Gly Ala Asp Thr Thr Ala Thr Asp Ile
                    885                 890                 895

Ile Cys Pro Met Tyr Ala Arg Val Asp Glu Asp Gln Pro Phe Pro Ala
                    900                 905                 910

Val Pro Lys Trp Ser Ile Lys Lys Trp Leu Ser Leu Pro Gly Glu Thr
                915                 920                 925

Arg Pro Leu Ile Leu Cys Glu Tyr Ala His Ala Met Gly Asn Ser Leu
                930                 935                 940

Gly Gly Phe Ala Lys Tyr Trp Gln Ala Phe Arg Gln Tyr Pro Arg Leu
945                 950                 955                 960
```

-continued

```
Gln Gly Gly Phe Val Trp Asp Trp Val Asp Gln Ser Leu Ile Lys Tyr
                965                 970                 975

Asp Glu Asn Gly Asn Pro Trp Ser Ala Tyr Gly Gly Asp Phe Gly Asp
            980                 985                 990

Thr Pro Asn Asp Arg Gln Phe Cys Met Asn Gly Leu Val Phe Ala Asp
        995                 1000                1005

Arg Thr Pro His Pro Ala Leu Thr Glu Ala Lys His Gln Gln Gln
        1010                1015                1020

Phe Phe Gln Phe Arg Leu Ser Gly Gln Thr Ile Glu Val Thr Ser
        1025                1030                1035

Glu Tyr Leu Phe Arg His Ser Asp Asn Glu Leu Leu His Trp Met
        1040                1045                1050

Val Ala Leu Asp Gly Lys Pro Leu Ala Ser Gly Glu Val Pro Leu
        1055                1060                1065

Asp Val Ala Pro Gln Gly Lys Gln Leu Ile Glu Leu Pro Glu Leu
        1070                1075                1080

Pro Gln Pro Glu Ser Ala Gly Gln Leu Trp Leu Thr Val Arg Val
        1085                1090                1095

Val Gln Pro Asn Ala Thr Ala Trp Ser Glu Ala Gly His Ile Ser
        1100                1105                1110

Ala Trp Gln Gln Trp Arg Leu Ala Glu Asn Leu Ser Val Thr Leu
        1115                1120                1125

Pro Ala Ala Ser His Ala Ile Pro His Leu Thr Thr Ser Glu Met
        1130                1135                1140

Asp Phe Cys Ile Glu Leu Gly Asn Lys Arg Trp Gln Phe Asn Arg
        1145                1150                1155

Gln Ser Gly Phe Leu Ser Gln Met Trp Ile Gly Asp Lys Lys Gln
        1160                1165                1170

Leu Leu Thr Pro Leu Arg Asp Gln Phe Thr Arg Ala Pro Leu Asp
        1175                1180                1185

Asn Asp Ile Gly Val Ser Glu Ala Thr Arg Ile Asp Pro Asn Ala
        1190                1195                1200

Trp Val Glu Arg Trp Lys Ala Ala Gly His Tyr Gln Ala Glu Ala
        1205                1210                1215

Ala Leu Leu Gln Cys Thr Ala Asp Thr Leu Ala Asp Ala Val Leu
        1220                1225                1230

Ile Thr Thr Ala His Ala Trp Gln His Gln Gly Lys Thr Leu Phe
        1235                1240                1245

Ile Ser Arg Lys Thr Tyr Arg Ile Asp Gly Ser Gly Gln Met Ala
        1250                1255                1260

Ile Thr Val Asp Val Glu Val Ala Ser Asp Thr Pro His Pro Ala
        1265                1270                1275

Arg Ile Gly Leu Asn Cys Gln Leu Ala Gln Val Ala Glu Arg Val
        1280                1285                1290

Asn Trp Leu Gly Leu Gly Pro Gln Glu Asn Tyr Pro Asp Arg Leu
        1295                1300                1305

Thr Ala Ala Cys Phe Asp Arg Trp Asp Leu Pro Leu Ser Asp Met
        1310                1315                1320

Tyr Thr Pro Tyr Val Phe Pro Ser Glu Asn Gly Leu Arg Cys Gly
        1325                1330                1335

Thr Arg Glu Leu Asn Tyr Gly Pro His Gln Trp Arg Gly Asp Phe
        1340                1345                1350

Gln Phe Asn Ile Ser Arg Tyr Ser Gln Gln Gln Leu Met Glu Thr
        1355                1360                1365
```

```
Ser His Arg His Leu Leu His Ala Glu Glu Gly Thr Trp Leu Asn
    1370            1375            1380

Ile Asp Gly Phe His Met Gly Ile Gly Gly Asp Asp Ser Trp Ser
    1385            1390            1395

Pro Ser Val Ser Ala Glu Phe Gln Leu Ser Ala Gly Arg Tyr His
    1400            1405            1410

Tyr Gln Leu Val Trp Cys Gln Lys
    1415            1420

<210> SEQ ID NO 2
<211> LENGTH: 80
<212> TYPE: PRT
<213> ORGANISM: Artificial
<220> FEATURE:
<223> OTHER INFORMATION: Synthetic fragment

<400> SEQUENCE: 2

Met Gln Lys Gln Pro Thr Trp Val Pro Asp Ser Glu Ala Pro Asn Cys
1               5                   10                  15

Met Asn Cys Gln Val Lys Phe Thr Phe Thr Lys Arg Arg His His Cys
                20                  25                  30

Arg Ala Cys Gly Lys Val Phe Cys Gly Val Cys Cys Asn Arg Lys Cys
            35                  40                  45

Lys Leu Gln Tyr Leu Glu Lys Glu Ala Arg Val Cys Val Val Cys Tyr
        50                  55                  60

Glu Thr Ile Ser Lys Ala Gln Ala Phe Glu Arg Gln Leu Phe Glu Leu
65                  70                  75                  80

<210> SEQ ID NO 3
<211> LENGTH: 54
<212> TYPE: PRT
<213> ORGANISM: Artificial
<220> FEATURE:
<223> OTHER INFORMATION: synthetic

<400> SEQUENCE: 3

Gly Gly Gly Gly Ser Gly Gly Gly Gly Ser Leu Glu Asp Ser Leu Ala
1               5                   10                  15

Val Val Leu Gln Arg Arg Asp Trp Glu Asn Pro Gly Val Thr Gln Leu
                20                  25                  30

Asn Arg Leu Ala Ala Arg Pro Pro Phe Ala Ser Trp Arg Asn Ser Glu
            35                  40                  45

Glu Ala Arg Thr Asp Arg
        50
```

WILD-TYPE RECEPTOR ASSAYS

CROSS-REFERENCE TO RELATED APPLICATIONS

This application claims priority from U.S. Provisional Patent Application No. 61/152,124, filed Feb. 12, 2009, which is hereby incorporated by reference in its entirety.

STATEMENT OF GOVERNMENTAL SUPPORT

None.

REFERENCE TO SEQUENCE LISTING, COMPUTER PROGRAM, OR COMPACT DISK

Applicants assert that the text copy of the Sequence Listing is identical to the Sequence Listing in computer readable form found on the accompanying computer file. Applicants incorporate the contents of the sequence listing by reference in its entirety.

BACKGROUND OF THE INVENTION

1. Field of the Invention

The present invention relates to the field of evaluation of agonists or antagonists of wild-type receptors, i.e., cellular receptors that have not been chemically or genetically modified for assay purposes.

2. Related Art

Presented below is background information on certain aspects of the present invention as they may relate to technical features referred to in the detailed description, but not necessarily described in detail. That is, individual parts or methods used in the present invention may be described in greater detail in the materials discussed below, which materials may provide further guidance to those skilled in the art for making or using certain aspects of the present invention as claimed. The discussion below should not be construed as an admission as to the relevance of the information to any claims herein or the prior art effect of the material described. G protein-coupled receptors (GPCRs) form one of the largest families of integral membrane receptors. GPCRs transduce information provided by extracellular stimuli into intracellular second messengers via their coupling to heterotrimeric G proteins and the subsequent regulation of a variety of effector systems. Therapeutic agents often target GPCRs because of their capability to bind ligands, hormones, and drugs with high specificity. Agonist activation of GPCRs also initiates processes that desensitize GPCR responsiveness and their internalization.

Common to most GPCRs is the cyclic process of signaling, desensitization, internalization, resensitization, and recycling to the plasma membrane. This cycle prevents cells from undergoing excessive receptor stimulation or periods of prolonged inactivity. Mechanisms for desensitization of GPCRs include receptor phosphorylation and subsequent endocytosis, which removes the receptor-ligand complex from the cell surface. As a result of this desensitization process, a common limitation of GPCR-targeted compositions is target organism tolerance or resistance, as receptor desensitization can mute their effectiveness.

U.S. Pat. No. 7,235,374 describes mutant GPCRs incorporating serines and/or threonines in the C-terminal region of the GPCR and using β-galactosidase fragments for detection. See also, as illustrative of activity in the field, Hammer, et al. 2007, *FASEB J.* 21, 3827-34; Molinari, et al. 2008, *Biochem.*
*J.* 409, 251-61; Hamdan, et al. 2007, *J. Biol. Chem.* 282, 29089-100; Garippa, et al. 2006 *Methods Enzymol.* 414, 99-120; and Yan, et al. 2002 *J. Biomol. Screen.* 7, 451-9.

SUMMARY OF THE INVENTION

The following brief summary is not intended to include all features and aspects of the present invention, nor does it imply that the invention must include all features and aspects discussed in this summary The present invention comprises, in certain aspects, a method for determining activation of a cell surface receptor, said cell surface receptor being one which binds to an intracellular binding partner and endocytoses with the intracellular binding partner in association with an endosome. The method further measures endocytosis of the receptor or other cell surface protein, and can be used to measure recycling of the cell surface protein from the cell surface to be returned or degraded. The method comprises the step of providing a cell expressing (i) a fusion protein of a fragment of β-galactosidase fused to the intracellular binding partner, (ii) a fusion protein of a fragment of β-galactosidase fused to an endosome-associated protein portion, wherein said fragments of β-galactosidase binding each other to form an active enzyme when in proximity in the cell and (iii) the cell surface receptor. The method also comprises a step of contacting the receptor on the cell with an agent that activates and thereby causes endocytosis of the receptor. This is referred to as a ligand, and is contacted for sufficient time for said ligand to bind to said receptor and any binding of said intracellular binding partner to said receptor to occur. The method then comprises steps which measure enzyme complementation and resultant formation of active β-galactosidase by movement of the receptor complex to the endosome, namely lysing said cells with a lysing medium comprising a substrate for said β-galactosidase that produces a detectable product; and determining said detectable product, wherein production of said detectable product indicates endosomal localization of said receptor.

In certain aspects of the invention, the endosome-associated protein is a binding fragment of endofin, in that it binds to the endosome, and in particular embodiments, a molecule on the membrane surface of the endosome. The cell used for the assay may be a Chinese Hamster ovary (CHO cell).

In certain aspects of the invention, the method uses a receptor that becomes phosphorylated upon activation, and said binding partner is a protein that comprises a domain that specifically binds to the phosphorylated form of the cell surface receptor.

The enzyme complementation fragment fused to said endosome-associated protein may be a small fragment of from about 36 to 60 amino acids of β-galactosidase. Such fragments may be weakly binding to the larger fragment.

Said cell surface receptor and said intracellular binding partner may be selected from the group consisting of GPCR and arrestin, and tyrosine kinase and Hrs protein.

In certain aspects of the invention, there is proved a method for determining activation by a ligand of GPCRs, specifically GPCRs of a type that bind to arrestin upon activation and endocytose in association with an endosome, said method comprising the steps of (a) providing cells expressing (i) a fusion protein of a fragment of β-galactosidase with arrestin, (ii) a complementary fragment of β-galactosidase with an endosome-associated protein, and (iii) said GPCR, wherein said complementary fragments only weakly bind to each other; (b) contacting said cells with said ligand for sufficient time for said ligand to bind to said GPCR and any resultant binding of arrestin to said GPCR to occur; (c) lysing said cells with a lysing medium comprising a substrate for said β-galactosidase that produces a detectable product; and (d) determining said detectable product, wherein production of said detectable product indicates activation of said GPCR. The GPCR may be a type B or class B GPCR. It may be SSTR2, i.e., somatostatin receptor type 2, preferably human SSTR2.

In certain aspects of the invention, the method uses an endosome-associated protein portion which comprises the FYVE domain of endofin.

In certain aspects of the invention there is proved a kit for use in GPCR translocation assays. The kit may comprise a genetic construct, such as an expression vector, for transforming cells, said construct encoding arrestin fused to a fragment of β-galactosidase and the kit further comprising a genetic construct, which may be the same of different, encoding a complementary fragment of β-galactosidase (complementary to the first mentioned fragment) fused to an endosome-associated protein. The endosome-associated protein may be endofin. The kit may further comprise a genetic construct encoding a GPCR.

DESCRIPTION OF THE SPECIFIC EMBODIMENTS

The present invention involves measurement of the endocytosis of cell membrane proteins. Cellular membrane proteins fulfill many functions in transducing signals when ligand binds, acting as ion channels, binding to other proteins involving diapedesis, viral nucleic acid insertion, immune synapse, etc. For many receptors of clinical interest, upon binding to ligand, the cellular membrane receptor becomes endocytosed, so that the population at the surface may change in the presence of ligand or an agonist. These proteins are typically endocytosed to a greater degree after activation. The present method may be characterized in certain respects in that the cellular membrane protein, i.e., the receptor (or ion channel or the like) used is "wild type," i.e., unlabeled or structurally unaltered for purposes of measurement in an assay. The labels that are used, which are fragments used in an enzyme fragment complementation assay, are attached so that one fragment is linked an auxiliary protein that binds to the receptor and is carried with the receptor as it is endocytosed, and a second enzyme fragment that is attached to a surface protein on the endosome.

Many of cell surface receptors upon binding to ligand bind to an auxiliary protein and endocytose and become associated with an endosome. Such cell surface receptors include the G protein coupled receptors ("GPCRs"); receptor tyrosine kinases, such as EGFR, that associate with proteins that bind specifically to the phosphorylated forms of the receptor and then are endocytosed, where typically these adapter proteins contain SH2 domains or protein tyrosine binding domains; cytokine receptors, typically phosphorylated by cytosolic kinases and binding to protein tyrosine binding domains; and the like. The largest and most important class of receptors of interest for pharmaceutical therapies are the GPCRs.

Figure 1:
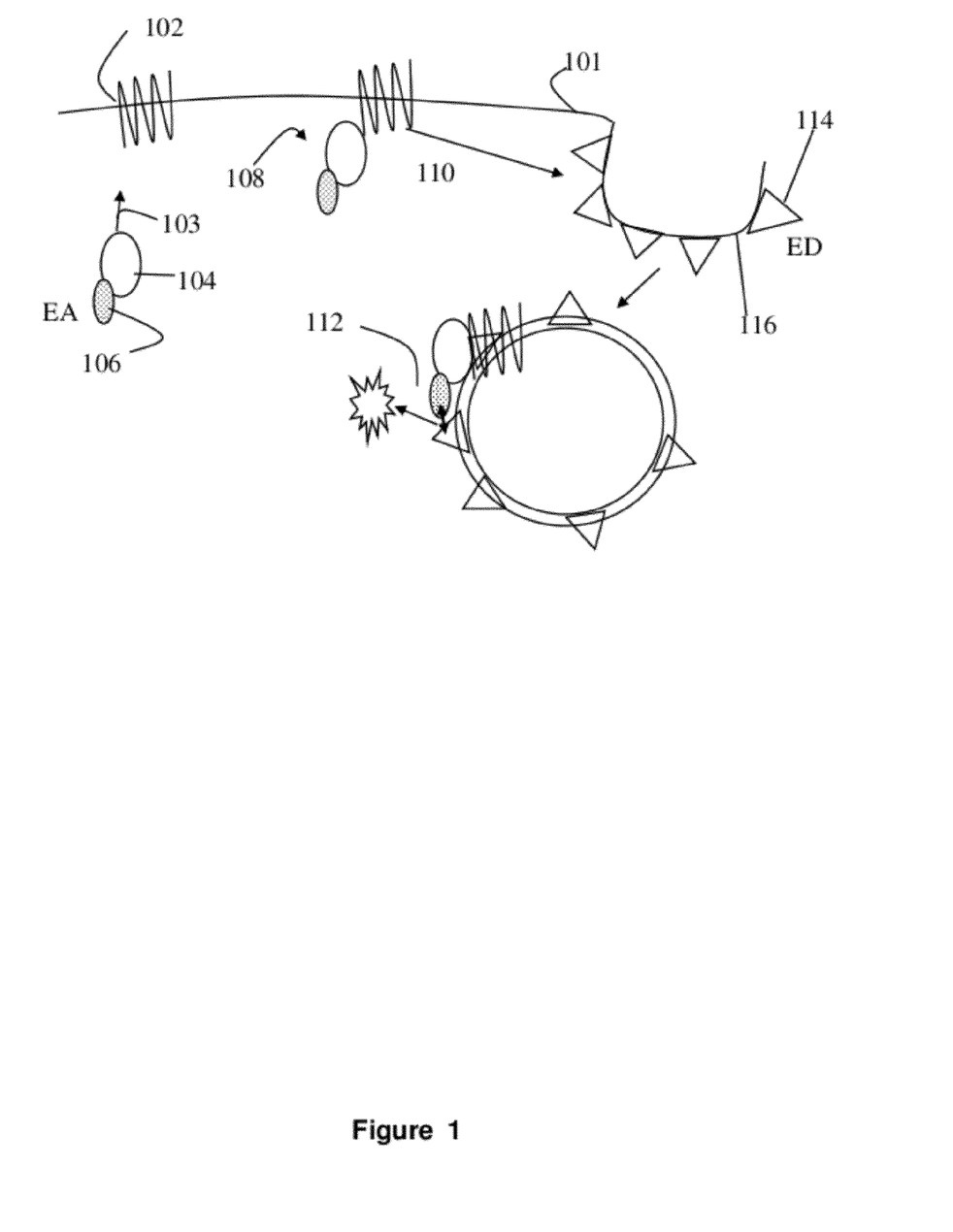
FIG. 1 is a schematic representation of an embodiment of the present invention.

The principles of the present assay are illustrated in FIG. 1. As shown in FIG. 1, a cell membrane such as the outer plasma membrane 101 of a eukaryotic cell contains embedded therein a number of cell membrane proteins, one of which is shown as a seven helix receptor 102. The receptor 102 is activated, e.g., by a test compound, or may be activated in other ways, such as in competition between a native agonist and a test compound. As is known, the activated receptor 102 recruits, upon activation an accessory protein 104; this protein is engineered to carry with it an enzyme fragment 106, preferably the enzyme acceptor (EA) of an enzyme fragment complementation pair. As shown by arrow 103, the accessory protein proceeds to bind to the receptor on the cytoplasmic domain of the receptor, as shown at 108. Then, as shown at 110, the complex translocates to an endosome 116, by a process such as receptor-mediated endocytosis.

Receptor-mediated endocytosis (RME), also called clathrin-dependent endocytosis, is a process by which cells internalize molecules (endocytosis) by the inward budding of plasma membrane vesicles containing proteins with receptor sites specific to the molecules being internalized. After the binding of a ligand to plasma membrane spanning receptors, a signal is sent through the membrane, leading to membrane coating, and formation of a membrane invagination. The receptor and its ligand are then opsonized in clathrin-coated vesicles. Once opsonized, the clathrin-coated vesicle uncoats (a pre-requisite for the vesicle to fuse with other membranes) and individual vesicles fuse to form the early endosome. Since the receptor is internalized with the ligand, the system is saturable and uptake will decline until receptors are recycled to the surface.

Referring again to FIG. 1, an endosome 116 in the cell has been engineered to express and enzyme donor 114. As shown, the ED 114 is expressed near the surface of the developing endosome. In this way, when the complex of the receptor, auxiliary protein and EA translocates as shown at 112 to the endosome, an active enzyme is formed by complexing of ED and EA. This active enzyme is allowed to act upon a substrate to produce a signal 112 indicative of the complexation and translocation. Preferably the signal will result from action of the active β-galactosidase on a chemiluminescent substrate.

DEFINITIONS

The terminology employed herein follows standard, accepted usage in the field. For further clarification, the following terms are further defined.

The phrase "cell surface receptor that binds to an intracellular binding partner" refers generally to a protein on the surface of a cell, preferably a eukaryotic cell, that serves as a receptor in the sense of recognizing a specific ligand, and, further, that operates through binding to a second molecule that forms a complex with the receptor under certain conditions, such as receptor activation. Thus, the term includes cell surface proteins such as G coupled protein receptors (GPCR) (where the intracellular binding partner may be arrestin), tyrosine kinase receptors such as EGF receptor (where the intracellular binding partner may be mu2 subunit of AP2 adaptors), and PDGF receptors (which bind cofactors and subsequently activate signal transduction, for example, through the PI3K pathway). Other potentially useful cell surface receptors include FLT4, FLK-2, etc., as well as ion channels.

The term "endosome-associated protein," as used herein, means a protein that is found in an endosome in the vicinity of an exposed area of the endosome, the endosome having a protein complex which is being or has been taken up by the endosome. It may be in certain instances associated with the endosome, i.e., loosely bound to one surface of a membrane, but not integrated into the hydrophobic region. It may be part of an early endosome. As is known, endosomes comprise three different compartments, early endosomes, late endosomes and recycling endosomes. They are distinguished by the time it takes for endocytosed material to reach them, and by markers such as rabs. Examples of endosome-associated proteins given below include Rab5 and endofin. Endofin, encoded by the ZFYVE16 gene, is an endosomal protein implicated in regulating membrane trafficking. It is characterized by the presence of a phosphatidylinositol 3-phosphate-binding FYVE domain positioned in the middle of the molecule. The FYVE domain is a conserved sequence present in more than 30 proteins in species from yeast to mammals. The major functional role of the FYVE domain proteins characterized thus far is membrane trafficking. Endosome-associated proteins used herein may include early endosome, which consist of a dynamic tubular-vesicular network (vesicles up to 1 μm in diameter with connected tubules of approx. 50 nm diameter). Markers (endosome-associated proteins) include RAB5 and RAB4, transferrin and its receptor and EEA1. They may include late endosomes, also known as MVBs, which are mainly spherical, lack tubules, and contain many close-packed lumenal vesicles. Endosome-associated proteins include RAB7 and RAB9 and mannose 6-phosphate receptors. They may also include recycling endosomes, which are concentrated at the microtubule organizing center and consist of a mainly tubular network, and have as an endosomal associated protein RAB1.

The term "weakly binds" in connection with binding of enzyme fragments to each other in EFC is known in the art and exemplified in US 20070275397 by Wehrman et al., published Nov. 29, 2007, entitled "Detection of molecular interactions using a reduced affinity enzyme complementation reporter system." Specific illustrative ED sequences are given there. As described there, the first and second β-galactosidase fragments are ones that have a low affinity for each other, where the low affinity is sufficient to provide for differing interaction dependent activity levels. As the fragments of the signal producing system have a low affinity for each other, the activity level (as determined using the assay reported in the Experimental Section below) that is observed from the system made up of the fragments in the absence of a polypeptide interaction of interest is less than the activity level that is observed in the absence of an interaction of interest with the β-galactosidase complementation system reported in Langley et al., *Proc. Nat'l Acad. Sci. USA* (1975) 72: 1254-1257.

The term "FYVE domain" as used herein means a protein domain also known as the FYVE zinc finger, named after four proteins that it has been found in: Fab1, YOTB/ZK632.12, Vac1, and EEA1. The FYVE domain has been shown to bind two zinc ions, and has eight potential zinc coordinating cysteine positions. Many members of this family also include two histidines in a motif R+HHC+XCG, where + represents a charged residue and X any residue. FYVE-type domains are divided into two known classes: FYVE domains that specifically bind to phosphatidylinositol 3-phosphate in lipid bilayers and FYVE-related domains of undetermined function. Those that bind to phosphatidylinositol 3-phosphate are often found in proteins targeted to lipid membranes that are involved in regulating membrane traffic. Most FYVE domains target proteins to endosomes by binding specifically to phosphatidylinositol-3-phosphate at the membrane surface. Consensus sequences may be obtained from http(colon slash slash) smart.embl-heidelberg.de/smart/show_info.p1.

The FYVE domain of endofin is the FYVE domain, as described above, of the protein endofin, encoded in humans by the gene ZFYVE16. It is described further in Seet et al., "Endofin recruits clathrin to early endosomes via TOM1.," *J. Cell. Sci.*, 2005 Feb. 1; 118(Pt 3):575-87. Epub 2005 Jan. 18.

The term "SSTR2" as used herein refers to the gene and protein for the human somatostatin receptor type II. The sequence may be found at UniProtKB/Swiss-Prot P30874. The C-terminus interacts with SHANK1 PDZ domain.

G Protein Coupled Receptors ("GPCRs") and Arrestin Binding

GPCRs are a large class of seven transmembrane domain receptors that transduce signals from outside the cells when bound to an appropriate ligand. The GPCRs have a myriad of functions, being involved in sensory perceptions, such as odor and vision, responding to pheromones, hormones and neurotransmitters, where the ligands greatly vary in nature and size. The GPCRs can affect behavior and mood, the immune system, the sympathetic and parasympathetic nervous system, cell density sensing and there may be additional physiological activities that involve GPCRs in their pathway. The GPCRs are associated with a number of diseases and have been an active target of pharmaceutical companies.

GPCRs are activated by an external signal resulting in a conformational change. It appears that once the receptor becomes bound it activates the G protein, which G protein is bound to ATP. The G protein is a trimer, which upon activation converts GTP to GDP. Active GPCRs are phosphorylated by protein-coupled receptor kinases. In many cases upon phosphorylation, the phosphorylated receptor becomes linked to arrestin. The binding to arrestin may result in translocation of the GPCR or other outcome.

GPCRs can exist as monomers, dimers, or heterodimers, when expressed in mammalian cells. The ability of GPCRs to form heterodimers provides a novel mechanism of cellular signaling. Two GPCRs that heterodimerize or one GPCR and a receptor that binds to the GPCR can attain signaling functions and ligand binding functions that are distinct from when only one of the receptors is present in a cell. As indicated above, the GPCRs are important to the functioning of a cell. Where the GPCR activation results in the regulation of another GPCR expressed on the same cell, there is interest in being able to detect and modulate the dimer- or oligomerization. By inhibiting the complexing of the GPCR with another membrane protein necessary for signal transduction, one can affect the pathway(s) regulated by the GPCR and the path way(s) affected by the second membrane protein. There is substantial interest in determining the effect of ligand binding to a GPCR, as well as the formation of a heterodimeric GPCR, complex on cell pathways.

In view of the importance of the GPCRs on the physiological status of mammals, there has been substantial interest in developing compounds that can modulate the activity of specific GPCRs and the interaction of GPCRs with other proteins in the cellular membrane and in the cytosol. As part of this process, compounds are screened as to their ability to induce the binding of arrestin to the GPCRs. One technique that has been employed to assay the affect of a candidate ligand is enzyme fragment complementation ("EFC"), where the two enzyme fragments may be fused to two different proteins. When the two proteins complex, the two enzyme fragments are brought together to form an active enzyme. This technique has been exploited in U.S. patent application nos. 2007/0275397 ("Detection of Molecular Interactions Using a Reduced Affinity Enzyme Complementation Reporter System," Nov. 29, 2007); 2005/0287522 ("Detection of Protein Translocation by Beta-Galactosidase Reporter Fragment Complementation," Dec. 29, 2005); and 2003/0175836 ("Detection of Molecular Interactions by Beta-Lactamase Reporter Fragment Complementation," Sep. 18, 2003). However, these techniques have relied on labeling the GPCR. Since the GPCR is involved in a number of binding events, the ligand, the G protein, dimerization or heterodimerization with another protein, the presence of the label adds uncertainty to the effectiveness of a ligand. It would be very valuable to have diagnostic assays where the GPCR is wild-type, rather than a labeled receptor.

The preferred GPCRs are those that are endocytosed to an endosome upon agonist binding, while bound to arrestin, where the endosome has an endosome binding protein associated with the endosome. The method employs enzyme fragment complementation, particularly using known fragments of β-galactosidase, where one fragment is fused with arrestin and the other fragment is fused with a protein associated with endosomes, particularly endofin. The fragments have a low binding affinity for each other. Cells are transformed with constructs encoding the fusion proteins, and may also be transformed with the wild-type GPCR, as needed. The resulting transformants are grown in an appropriate medium and then subjected to a candidate compound for determining agonist or antagonist (a known agonist is used for screening for antagonists) and the assay mixture incubated for sufficient time for any reaction to occur. In case of the unavailability of a β-galactosidase substrate that provides a detectable product internal to the cell, the cells are lysed and substrate added to the lysate. The signal may then be read in accordance with the nature of the product of the β-galactosidase enzyme reaction.

The most commonly used system of classification for GPCRs is that implemented in the GPCRDB database, which may be found on the world wide web at gpcr-dot-org. It divides the GPCRs into six classes (Class A: Rhodopsin-like, with over 80% of all GPCRs in humans; Class B: Secretin-like; Class C: Metabotropic glutamate receptors; Class D: Pheromone receptors; Class E: cAMP receptors; and the much smaller Class F: Frizzled/smoothened family). Classes A, B, C and F are found in mammalian species while Class D proteins are found only in fungi and Class E proteins are exclusive to Dictyostelium. The six classes are further divided into sub-divisions and sub-sub-divisions based on the function of a GPCR and its specific ligand. Exemplary GCPRs for use in the present invention include CXCR4 and CCR5, (related to HIV entry).

Exemplary class B GPCRs for use in the present assay include secretin, calcitonin, parathyroid hormone/parathyroid hormone-related peptides and vasoactive intestinal peptide receptors, all of which activate adenylyl cyclase and the phosphatidyl-inositol-calcium pathway.

There are different mechanisms by which the GPCRs become desensitized. For the majority, the receptors are endocytosed with arrestin bound and form endosomes, endosome-forming proteins, e.g., endofin, being bound to the endosome membrane. While other classes of GPCRs are reported to separate from arrestin during endocytosis, in many cases the arrestin is retained for sufficient time to allow the subject assay to be performed. It will be either necessary to know or determine whether the subject assay is applicable to a particular GPCR before employing the subject assay to screen GPCR ligands, i.e., agonists or antagonists.

Other Membrane-Bound Proteins Subject to Endocytosis while Bound to Auxiliary Proteins As mentioned above, the present methods may be adapted, given the present teachings, for use with other cell surface receptors beyond the GPCRs. These include the receptor tyrosine kinases, which bind to auxiliary proteins such as GRB2 and SOS (Details in Mukherjee et al., "Vesicular trafficking of tyrosine kinase receptors and associated proteins in the regulation of signaling and vascular function," *Circ Res.*, 2006 Mar. 31; 98(6):743-56). Tyrosinase receptors also bind to HRS. See, Lloyd et al.,"Hrs Regulates Endosome Membrane Invagination and Tyrosine Kinase Receptor Signaling in Drosophila," *Cell*, Volume 108, Issue 2, January 2002, Pages 261-269.

Also included are ion channels, which bind e.g., to ubiquitin (Details in Robertson, Endocytic control of ion channel density as a target for cardiovascular disease," *J. Clin. Invest.*, 2009; 119(9):2531-2534).

Enzyme Fragment Complementation

In accordance with the subject invention ligands for binding to wild-type receptors are screened using an enzyme fragment complementation ("EFC") assay. The wild-type receptors are characterized by being cell-surface receptors, upon binding to an agonist, usually undergo phosphorylation, complex with an auxiliary protein, endocytose associated with an endosome, wherein the endosome is associated with an endosome binding protein. Receptors that come within this category include GPCRs, receptor tyrosine kinases, cytokine binding receptors, etc. Since the GPCRs are the largest and most important class of receptors coming within this group, they will be discussed in detail as exemplary of the group. By employing the subject methodology, the receptor and ligand can be used unmodified, so that there is no intrinsic interference with the binding of the receptor and its ligand, where the ligand may be an agonist or antagonist. In considering the following description, it should be understood that the GPCR may be replaced with the other types of receptors and arrestin may be replaced with the auxiliary proteins associated with the particular receptor.

EFC Fusion Proteins and Constructs

Generally speaking, the subject invention, in certain aspects, provides a method for screening binding of a cell surface receptor such as a GPCR to a ligand such as a GPCR ligand employing a β-galactosidase enzyme fragment complementation assay, using an enzyme donor fragment ("ED") and an enzyme acceptor fragment ("EA"). Employed in the method is a first fusion protein comprising (a) an arrestin linked to a fragment of β-galactosidase (such as EA) optionally joined by a linking group. Also employed is a second fusion protein comprising an endosome-associated protein, e.g., endofin, linked to the complementary fragment of β-galactosidase (e.g., ED), where when arrestin is bound to said endosome by means of the GPCR being with the endosome, a functional β-galactosidase is formed. For the most part, mammalian cells are transformed with genetic constructs expressing the first and second fusion proteins. In the present methods, the β-galactosidase fragments are linked, respectively, to a surface protein on the endosome and to an auxiliary protein that binds to the receptor under study as a result of ligand binding to the receptor, exemplified by arrestin binding to GPCRs. This is accomplished by transfecting cells with expression constructs encoding these proteins, as is known in the art. The DNA sequences may be further engineered to include linkers between the EA/ED and the fusion partner, and may also be used to modify the native fusion partner by shortening or stabilizing it, as described below.

One fragment, preferably the EA, is linked to an auxiliary protein which binds to the cell surface receptor. The auxiliary protein may be the intact protein or may only be the binding domain of the auxiliary protein or some protein in between. In many cases it will be sufficient to have the binding domain only, which may allow for simpler synthesis of the expression construct, so long as the binding affinity is not overly compromised.

The second fragment, preferably the ED, is linked to an endosomal surface protein. There are a number of proteins that are associated with endosomes. These proteins include endofin, Rab5 (See Genbank RAB5A), Genbank symbol EEA1, HRS (See Genbank HGS), and the majority of phosphatidyl-inositol 3-phosphate binding proteins.

The small fragment of β-galactosidase ("ED") may have the naturally occurring sequence or a mutated sequence. Of particular interest are small fragments of from about 36 to 60, more usually not more than about 50, amino acids. Desirably, the ED has a low affinity for the large fragment of β-galactosidase ("EA"), so that there is little complexation between the large and small fragments in the absence of recruitment of the complementing β-galactosidase fragment to endosomes, that is, the signal observed with the small fragment is at least about 50%, more usually at least about 70%, less than the signal observed with the commercially available fragment of 90 amino acids, when the two fragments are combined in the absence of fusion with other proteins. For further description of the small fragments, see U.S. Pat. No. 7,135,325. For further description of mutated EDs, see U.S. patent application publication no. 2007/0275397, both of which references are incorporated herein in their entirety as if set forth herein. The mutated ED will desirably have less than about 0.5, but at least about 0.1, of the activity of the wild-type sequence in the assay of interest or an analogous assay. For increasing affinity between the ED and EA, EDs will be used and free of mutations from the wild-type sequence.

The ED will usually be linked to the C-terminus of the endosome-associated protein. The ED will come from the N-terminus proximal region of the β-galactosidase enzyme. The fusion proteins provide a functional protein that is soluble, does not aggregate so as to be unavailable for complexing, has substantially the natural folding, so as to be susceptible to binding to endogenous proteins and molecules that normally complex to the polypeptide fused to the ED, and will usually be able to perform substantially the same functions that such polypeptide performs. Therefore, the polypeptide is capable of acting as a surrogate for the natural protein to allow for measurements that are predictive of the activity of the natural protein.

The ED may be joined to the coding region in a variety of ways. For a cDNA gene, one may select a suitable restriction site for insertion of the sequence, where by using overhangs at the restriction site, the orientation is provided in the correct direction. By using a plasmid in yeast having the cDNA gene, with or without an appropriate transcriptional and translational regulatory region, one may readily insert the ED construct so as to be fused to any linker(s) and the cDNA gene at an appropriate site.

Various conventional ways for inserting encoding sequences into a gene can be employed. For expression constructs and descriptions of other conventional manipulative processes, See, e.g., Sambrook, Fritsch & Maniatis, "Molecular Cloning: A Laboratory Manual," Second Edition (1989) Cold Spring Harbor Laboratory Press, Cold Spring Harbor, N.Y. (herein "Sambrook et al., 1989"); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins EDs. (1985)]; "Transcription And Translation" [B. D. Hames & S. J. Higgins, EDs. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Assay Methodology

In performing the method, the cells are incubated in an assay medium in a selected environment, normally including an agonist or agonist candidate, for sufficient time for any binding to occur, and, preferably, for endocytosis to reach equilibrium (typically about 90 min.), followed by the addition of a β-galactosidase substrate, which substrate results in a detectable signal, and then determining the signal as a measure of the binding. In some instances, one may study an antagonist for displacing or preventing binding of the agonist or a compound modulating the binding of the GPCR to the protein of interest.

The methods employ genetically modified cells, where the cells are modified with first and second genetic expression constructs and often a third (the third would be the analyte, in this case a GPCR). The method employs enzyme fragment complementation ("EFC") with β-galactosidase to detect the binding of arrestin to a GPCR. The method relies on a compound binding to a GPCR where arrestin fused to a member of the β-galactosidase enzyme fragment complementation ("EFC") pair binds to the GPCR. The GPCR and arrestin complex is then endocytosed where the resulting endosome comprises the fusion protein of the endosome related protein and the member of the EFC pair. The physical proximity of the two complementary fragments of β-galactosidase greatly enhances the enzymatic activity of the β-galactosidase as compared to when the two fragments are not bound together in physical proximity.

The assay is performed under conventional conditions. Depending upon the mode of the assay different selected environmental conditions will be employed. For studying ligands for a GPCR, the selected environment will include a candidate ligand for the GPCR to detect any resulting activity, which results in the complex of the GPCR and arrestin. After sufficient incubation time for the arrestin to be transported and bind to the GPCR, and the GPCR endocytosed, β-galactosidase substrate is added and the turnover of the substrate determined, where the substrate provides for a detectable product. If desired, the cells are lysed and the substrate added with or after the addition of the lysing reagent. The formation of the endosome is sufficiently stable as to be retained after lysis. The resulting signal is a measure of the activity of the candidate ligand.

Cells Used in Assay

Any eukaryotic cell may be employed, for the most part cell lines being employed. The cell lines will usually be mammalian, but for some purposes unicellular organisms or cells from non-vertebrates can be used. Mammalian cell lines include CHO, HeLa, MMTV, HepG2, HEK, U2OS and the like. The cells are genetically modified transiently or permanently, usually permanently. Various vectors that are commercially available can be used successfully to introduce the two, three or more expression constructs into the eukaryotic cell. For an extensive description of cell lines, vectors, methods of genetic modification, and expression constructs, see published US application serial no. 2003/0092070, Zhao, et al., May 15, 2003, paragraphs 00046-00066, which are also specifically incorporated herein by reference.

Transformed cells are cloned that have various expression levels of the fusion proteins. The best clone is then chosen by lowest EC50 and best signal to background ratio. The cells are transiently or permanently transformed, in the case of the former using a conventional vector, normally a viral vector, e.g., adenovirus or Moloney Murine Leukemia Virus. Methods include transfection, electroporation, microinjection, transduction, cell fusion, DEAE dextran, calcium phosphate precipitation, lipofection (lysosome fusion), use of a gene gun, using a viral vector, with a DNA vector transporter, and the like. For permanent insertion into the genome, various techniques are available for the insertion of the sequence in a homologous or non-homologous fashion. These techniques are well known. For random insertion, the introduction of the nucleic acid by any of the above methods will usually be sufficient. For homologous recombination, see, for example, U.S. Pat. Nos. 7,361,641, 5,578,461, 5,272,071 and PCT/US92/09627, and references cited therein.

Regulatory regions that may be used will be functional in the cell and may be obtained from cellular or viral genes. Illustrative regulatory regions include many promoters that are commercially available today. Expression of the fusion protein may be controlled by any promoter/enhancer element known in the art, but these regulatory elements must be functional in the host cell selected for expression. Promoters which may be used to control fusion gene expression include, but are not limited to, the SV40 early promoter region (Benoist and Chambon, 1981, *Nature*, 290:304-310), the promoter contained in the 3' long terminal repeat of Rous sarcoma virus (Yamamoto, et al., 1980, *Cell*, 22:787-797), the herpes thymidine kinase promoter (Wagner et al., 1981, *Proc. Natl. Acad. Sci. U.S.A.*, 78:1441-1445), the regulatory sequences of the metallothionein gene (Brinster et al., 1982, *Nature*, 296:39-42), etc.

The screening method involves growing the cells in an appropriate medium and then adding the candidate ligand. The medium is then incubated for at least about 0.25 h and not more than about 6 h, as a matter of convenience. The volume will generally not exceed about 250 μl, usually not more than about 200 μl, and generally be at least about 10 μl, more usually at least about 20 μl, where the volume of the candidate compound solution addition will generally dilute the cell medium less than about 1:1, usually not more than about 0.5:1. When the reagent is dry, there will be no dilution. After incubating the assay sample for about 0.25 to 6 h, a reagent solution for lysis of the cells and containing a detectable β-galactosidase substrate may be added to the assay sample and one or more readings taken of the product from the substrate. The ratio of dilution will be not more than about 1:2, usually in the ratio of about 1:0.25 to 1:2, more usually 1:1 and as little at 1:0.25 or less.

The following examples are offered by way of illustration and not by way of limitation.

EXPERIMENTAL

The following constructs were prepared as follows:
Arrestin-EA Fusion Protein:

The wild-type sequence of human Arrestin-B2 was PCR amplified and inserted into a retroviral expression vector that contains the EA β-galactosidase fragment using restriction sites engineered into the PCR primers. The Arrestin-B2 coding sequence was inserted so that upon transcription and translation it would produce a fusion of the Arrestin-B2 and EA proteins joined by a flexible GlySer linker.

Amino Acid Sequence of the Arrestin-B2-EA fusion protein. Arrestin-B2 is underlined, the linker is in Bold, and the EA sequence is italicized:

(SEQ ID NO: 1)
MGEKPGTRVFKKSSPNCKLTVYLGKRDFVDHLDKVDPVDGVVLVDPDYLK

DRKVFVTLTCAFRYGREDLDVLGLSFRKDL

FIATYQAFPPVPNPPRPPTRLQDRLLRKLGQHAHPFFFTIPQNLPCSVTL

QPGPEDTGKACGVDFEIRAFCAKSLEEKSH

KRNSVRLVIRKVQFAPEKPGPQPSAETTRHFLMSDRSLHLEASLDKELYY

HGEPLNVNVHVTNNSTKTVKKIKVSVRQYA

DICLFSTAQYKCPVAQLEQDDQVSPSSTFCKVYTITPLLSDNREKRGLAL

DGKLKHEDTNLASSTIVKEGANKEVLGILV

SYRVKVKLVVSRGGDVSVELPFVLMHPKPHDHIPLPRPQSAAPETDVPVD

TNLIEFDTNYATDDDIVFEDFARLRLKGMK

DDDYDDQLCGQLFELGGGGSGGGGSLES*MGVITDSLAVVARTDRPSQQLR*

*SLNGEWRFAWFPAPEAVPESWLECDLPEAD*

*TVVVPSNWQMHGYDAPIYTNVTYPITVNPPFVPTENPTGCYSLTFNVDES*

*WLQEGQTRIIFDGVNSAFHLWCNGRWVGYG*

*QDSRLPSEFDLSAFLRAGENRLAVMVLRWSDGSYLEDQDMWRMSGIFRDV*

*SLLHKPTTQISDFHVATRFNDDFSRAVLEA*

*EVQMCGELRDYLRVTVSLWQGETQVASGTAPFGGEIIDERGGYADRVTLR*

*LNVENPKLWSAEIPNLYRAVVELHTADGTL*

*IEAEACDVGFREVRIENGLLLLNGKPLLIRGVNRHEHHPLHGQVMDEQTM*

*VQDILLMKQNNFNAVRCSHYPNHPLWYTLC*

*DRYGLYVVDEANIETHGMVPMNRLTDDPRWLPAMSERVTRMVQRDRNHPS*

*VIIWSLGNESGHGANHDALYRWIKSVDPSR*

*PVQYEGGGADTTATDIICPMYARVDEDQPFPAVPKWSIKKWLSLPGETRP*

*LILCEYAHAMGNSLGGFAKYWQAFRQYPRL*

*QGGFVWDWVDQSLIKYDENGNPWSAYGGDFGDTPNDRQFCMNGLVFADRT*

*PHPALTEAKHQQQFFQFRLSGQTIEVTSEY*

*LFRHSDNELLHWMVALDGKPLASGEVPLDVAPQGKQLIELPELPQPESAG*

*QLWLTVRVVQPNATAWSEAGHISAWQQWRL*

*AENLSVTLPAASHAIPHLTTSEMDFCIELGNKRWQFNRQSGFLSQMWIGD*

*KKQLLTPLRDQFTRAPLDNDIGVSEATRID*

*PNAWVERWKAAGHYQAEAALLQCTADTLADAVLITTAHAWQHQGKTLFIS*

*RKTYRIDGSGQMAITVDVEVASDTPHPARI*

*GLNCQLAQVAERVNWLGLGPQENYPDRLTAACFDRWDLPLSDMYTPYVFP*

*SENGLRCGTRELNYGPHQWRGDFQFNISRY*

*SQQQLMETSHRHLLHAEEGTWLNIDGFHMGIGGDDSWSPSVSAEFQLSAG*

*RYHYQLVWCQK*

Endofin-ED Fusion Protein

Endofin-GFP-ProLink fusion protein (ProLink is a small fragment of β-galactosidase commercially available from DiscoveRx Inc., Fremont, Calif.). (GFP was included to provide an additional way to identify the presence of the fusion protein). Further details on endofin may be found at GenBank® entry ZFYVE16. Endofin, as discussed above, contains an FYVE zinc finger domain, containing zinc fingers and, in certain respects, providing a binding region.

Amino Acid sequence of the Endofin Fyve domain-ProLink Fusion is given below, and the FYVE domain of Endofin is underlined, the linker is in Bold, and the ProLink ED sequence, immediately following the bold sequence, is italicized.

(SEQ ID NO: 2)
MQKQPTWVPDSEAPNCMNCQVKFTFTKRRHHCRACGKVFCGVCCNRKCKL

QYLEKEARVCVVCYETISKAQAFERQLFEL (GFP coding sequence)

(SEQ ID NO: 3)
GGGGSGGGGSLEDSLAVVLQRRDWENPGVTQLNRLAARPPFASWRNSEEA

RTDR..

The parenthetical GFP coding sequence represents any green fluorescent protein construct. Thus is provided endofin FYVE-(GFP)-linker-ED. A GPCR may be separately expressed. The GFP is optional.

SEQ ID NO: 2 and SEQ ID NO: 3 are prepared as a continuous construct, with a GFP sequence in between, as indicated. The GFP sequence is used for monitoring the assay and is not necessary to the present signal detection. Endofin-prolink and arrestin-EA are expressed as separate fusion proteins.

The genetic constructions described were transformed into CHO cells as follows:

The GPCRs of interest were PCR amplified and inserted into a retroviral expression vector, including a stop codon immediately c-terminal to the coding region of the receptor. The vector also contains two antibiotic resistance genes. One for selection in bacterial cells for production of the plasmid, and one for mammalian cells that would allow selection of cells based on resistance to the corresponding antibiotic. Virus was produced from the resulting construct and used to infect the target CHO cells that were previously engineered to express the Arrestin-B2-EA fusion protein and the Endofin FYVE domain-GFP-Prolink fusion protein. The cells were selected in three antibiotics to ensure they maintained expression of all three genetic constructs.

The cells were screened and selection for the genetic constructs was as follows: 250 µg/ml hygromycin for the arrestin construct; 800 µg/ml neomycin for the endofin construct and 1 µg/ml puromycin for the SSTR2 construct.

Figure 2:
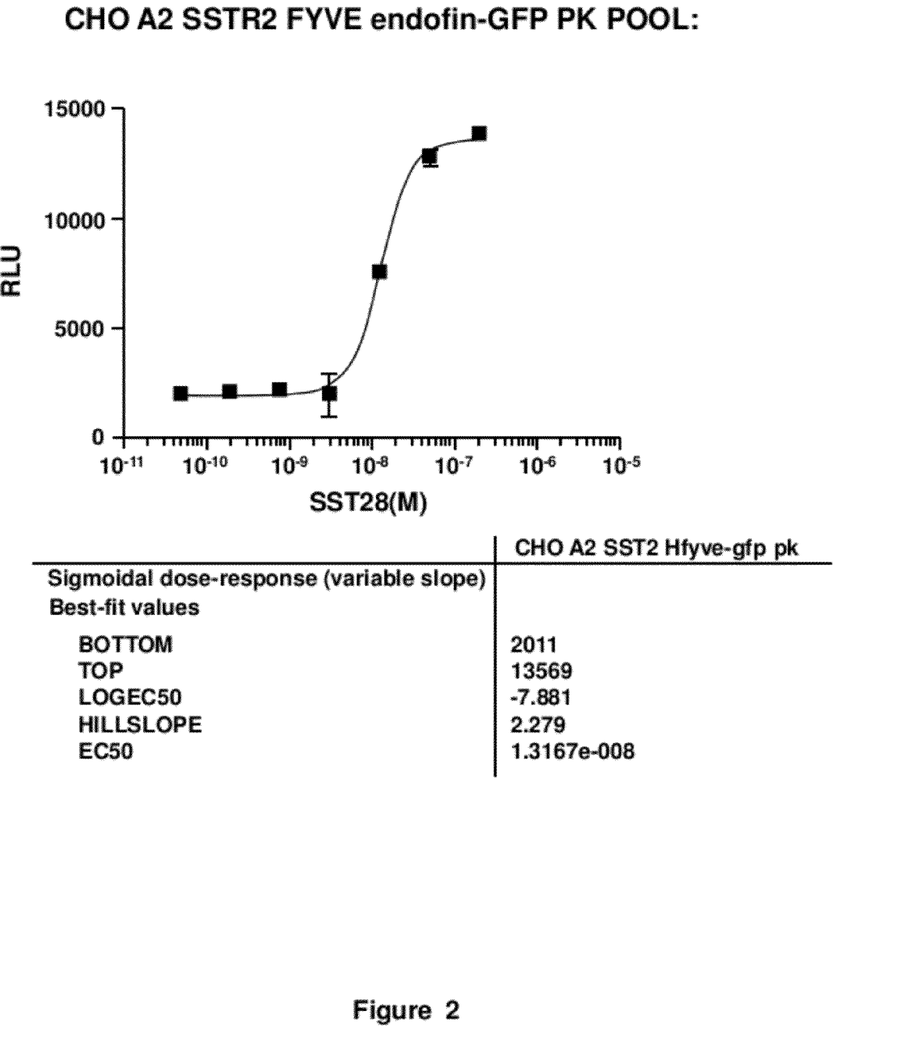
FIG. 2 is a graph showing a dose response curve of CHO cells expressing SSTR2 with somatostatin-28.

The assays were performed as follows: the transformed CHOA2 cells expressing somatostatin receptor 2 (SSTR2) were plated overnight in growth medium (Ham's F-12, 10% FBS, Pen/Strep) in 384 well opaque white plates. The candidate ligand somatostatin-28 was diluted in PBS-BSA and added to the cells at t=0. At t=3, PathHunter® detection reagent was added and the mixture incubated for 1 h at room temperature. The plates were read on a luminometer. The graph in FIG. 2 indicates the results.

It is evident from the above results that the subject assay provides a sensitive method for screening candidate compounds as agonists and antagonists for GPCRs that endocytose with arrestin upon agonist binding. It is found that a limited number of GPCRs endocytose complexed to arrestin; however, other GPCRs that are sequestered into endosomes retain the arrestin for sufficient time to permit the subject assay to be performed in a reproducible manner. The ability to use wild-type GPCRs avoids any interference that might result from using a labeled GPCR, where the label might interfere with the binding of a ligand and the ligand might interfere with the detection of the label.

Although the invention has been described with reference to the above examples, it will be understood that modifications and variations are encompassed within the spirit and scope of the invention. Accordingly, the invention is limited only by the following claims. All references referred to in the specification are incorporated by reference as if fully set forth therein. In accordance with 37 CFR 1.57, it is made explicit here that applicants intend to incorporate such referenced patents and publications listed and specifically identified above, as well as information pertaining to the recited GenBank® entries and corresponding genes and proteins and the sequences thereof.

What is claimed is:

1. A method for determining activation of a cell surface receptor that binds to an intracellular binding partner and endocytoses with the intracellular binding partner to associate with an endosome, comprising the steps of:

(a) providing a cell expressing (i) a fusion protein of a fragment of β-galactosidase fused to the intracellular binding partner, (ii) a fusion protein of a fragment of β-galactosidase fused to an endosome-associated protein portion, wherein said fragments of β-galactosidase weakly bind each other so that complementation activity depends on interaction of the fusion proteins, and (iii) the cell surface receptor, wherein the cell surface receptor is unlabeled;

(b) contacting said cell with a ligand for sufficient time for said ligand to bind to said receptor and any binding of said intracellular binding partner to said receptor to occur; then (c) lysing said cells with a lysing medium comprising a substrate for said β-galactosidase that produces a detectable product; and (d) determining said detectable product, wherein production of said detectable product indicates endosomal localization of said receptor.

2. A method according to claim 1, wherein said endosome-associated protein is a fragment of endofin binding to the endosome.

3. A method according to claim 1, wherein said cell is a CHO cell.

4. A method according to claim 1, wherein said receptor is phosphorylated upon activation and said binding partner is a protein that comprises a domain that specifically binds to the phosphorylated form of the cell surface receptor.

5. A method according to claim 1, wherein said fragment fused to said endosome-associated protein is a fragment of from 36 to 60 amino acids.

6. The method of claim 1 wherein said cell surface receptor and said intracellular binding partner are selected from the group consisting of GPCR and arrestin, tyrosine kinase and Hrs protein.

7. A method for determining activation by a ligand of an unlabeled GPCR, which binds to arrestin upon activation and endocytoses to associate with an endosome, said method comprising the steps of:
  (a) providing cells expressing (i) a fusion protein of a fragment of β-galactosidase with arrestin, (ii) a complementary fragment of β-galactosidase with an endosome-associated protein, and (iii) said unlabeled GPCR, wherein said complementary fragments weakly bind to each other so that complementation activity depends on interaction of the fusion proteins;
  (b) contacting said cells with said ligand for sufficient time for said ligand to bind to said GPCR and any resultant binding of arrestin to said GPCR to occur;
  (c) lysing said cells with a lysing medium comprising a substrate for said β-galactosidase that produces a detectable product; and
  (d) determining said detectable product, wherein production of said detectable product indicates activation of said GPCR.

8. A method according to claim 7, wherein said endosome-associated protein comprises the FYVE domain of endofin.

9. A method according to claim 7, wherein said cell is a CHO cell.

10. A method according to claim 7, wherein said GPCR is Type B.

11. A method according to claim 7, wherein said fragment fused to said endosome-associated protein is a fragment of from 36 to 60 amino acids.

12. A method according to claim 7, wherein said GPCR is SSTR2.

13. A kit for use in GPCR translocation assays, comprising a genetic construct encoding arrestin fused to a fragment of β-galactosidase and a genetic construct encoding a complementary fragment of β-galactosidase fused to an endosome-associated protein.

14. The kit of claim 13 where the endosome-associated protein is endofin.

15. The kit of claim 13 further comprising a genetic construct encoding a GPCR.

* * * * *